United States Patent [19]
Hoffmann

[11] Patent Number: 5,981,488
[45] Date of Patent: Nov. 9, 1999

[54] GLUCAGON-LIKE PEPTIDE-1 ANALOGS

[75] Inventor: James Arthur Hoffmann, Greenwood, Ind.

[73] Assignee: Eli Lillly and Company, Indianapolis, Ind.

[21] Appl. No.: 09/047,663

[22] Filed: Mar. 25, 1998

Related U.S. Application Data

[60] Provisional application No. 60/042,167, Mar. 31, 1997.

[51] Int. Cl.$^6$ .......................... A61K 38/26; C07K 14/605
[52] U.S. Cl. ............................ 514/12; 530/308; 530/324
[58] Field of Search ............................ 514/12; 530/308, 530/324

[56] References Cited

U.S. PATENT DOCUMENTS

| | | | |
|---|---|---|---|
| 4,347,374 | 8/1982 | Kollonitsch et al. | 548/344 |
| 5,118,666 | 6/1992 | Habener | 514/12 |
| 5,120,712 | 6/1992 | Habener | 514/12 |
| 5,614,492 | 3/1997 | Habener | 514/12 |
| 5,705,483 | 1/1998 | Golloway et al. | 514/12 |

FOREIGN PATENT DOCUMENTS

| | | |
|---|---|---|
| 619322A2 | 2/1994 | European Pat. Off. . |
| 619322A3 | 3/1996 | European Pat. Off. . |
| WO 91/11457 | 8/1991 | WIPO . |
| WO 92/18531 | 10/1992 | WIPO . |
| WO 93/18786 | 9/1993 | WIPO . |
| WO 93/25579 | 12/1993 | WIPO . |
| WO 95/05848 | 3/1995 | WIPO . |

OTHER PUBLICATIONS

Komatsu, R., et al., *Diabetes*, 38:902–905 (1989).
Orskov, C., et al., *J. Biol. Chem.*, 264(22):12826–12829 (1989).
Majsov, S., *Int. J. Peptide Protein Res.*, 40:333–343 (1989).
Holz, G.G., et al., *Nature*, 361:362–365 (1993).
Orskov, C., *Diabetologia*, 35:701–711 (1992).
Mentlein, R., et al., *Eur. J. Biochem.*, 214:829–835 (1993).
Handbook of Experimental Pharmacology, Springer–Verlag, Hasselblatt, et al., (Eds.), 32 (2):729–777 (1975).
Nauck, M.A., et al., *J. Clin. Invest.*, 91:301–307 (1993).
Nauck, M.A. et al., *Diabetologia*, 36:741–744 (1993).
Gutniak, M., et al., *N. E. J. Med.*, 326(20):1316–1322, (1992).
Thorens B., et al., *Diabetes*, 42:1219–1225 (1993).
Levine–Pinto, H. et al., *Biochem. Biophys. Red. Commun.*, 103 (4) :1121–1130 (1981).
Owa, T., et al., *Chem. Letters*: 873–874 (1988).
Altman, J., et al., *Synthetic Commun.*, 19(11 & 12) :2069–2076 (1989).
O'Donnell, J.J. et al., *Synthetic Commun.*, 19(7 & 8): 1157–1165 (1989).
Galloway, J.A., *Diabetes Care*, 13:1209–1239, (1990).
Galloway, J.A., et al., *Clin. Therap.*, 12:460–472, (1990).
Suzuki, S., et al., *Endocrinology*, 125, 3109–3114, (1990).
Ananthanancayanan, V.V., et al., *Mol. Biol. Cell* (Supp) 3, 250A 1452 (1992).
Epand, R.M., *Mol. Pharmacol.*, 22:105–108 (1982).
Pridal, L., et al., "Absorption of Glucagon–Like Peptide–1 Can Be Protracted by Zinc or Protamine", *International Journal of Pharmaceuticals*, 136 (1996) 53–59.

*Primary Examiner*—Bennett Celsa
*Attorney, Agent, or Firm*—Ronald S. Maciak

[57] ABSTRACT

The invention provides extended-action GLP-1 based peptides and compositions that are useful for treating diabetes and minimize the risk of hypoglycemia.

7 Claims, No Drawings

GLUCAGON-LIKE PEPTIDE-1 ANALOGS

This application claims the benefit of U.S. Provisional Application Ser. No. 60/042,167, filed Mar. 31, 1997.

FIELD OF INVENTION

The present invention relates to protein chemistry as applied to pharmaceutical research and development. The invention provides novel peptides and compositions that are useful for treating diabetes.

BACKGROUND OF THE INVENTION

The World Health Organization estimates that there may be as many of 103 million patients with type II diabetes worldwide, although only 23 million have been diagnosed and are receiving therapy. Type II diabetes (non-insulin dependent diabetes mellitus—NIDDM) is characterized by a resistance to insulin action in peripheral tissues such as muscle, adipose and liver and by a progressive failure in the ability of the islet β-cell to secrete insulin. Because current therapeutics do not halt the progression of β-cell failure, virtually all NIDDM patients eventually require insulin to control blood glucose levels. The most commonly described therapeutics for such patients are the sulfonylureas, so called oral agents, that stimulate insulin secretion. Each year, 10–20% of the patients on sulfonylureas fail to maintain acceptable blood glucose levels and switch to insulin therapy.

Insulin however, is a difficult drug for patients to self-administer for several reasons. First, insulin has a narrow therapeutic index. This leads to poor control of blood glucose levels since most patients and physicians prefer elevated glucose levels to the risk of hypoglycemia and coma. Second, proper insulin dosing is complicated. The insulin dose that a diabetic patient should administer is dependent on the amount of food consumed, the time between meals, the amount of physical exercise, and the prevailing blood glucose level which requires blood glucose monitoring to determine. The general diabetic population is ill-equipped to correlate these factors to the proper insulin dose. Third, as a parenteral product, insulin is inconvenient to administer. Alternative delivery methods are made even more difficult by the narrow therapeutic index for insulin. Thus, many diabetic patients lack good control of blood glucose.

The Diabetes Control and Complication Trial definitively established for Type I diabetics that disease complications (retinopathy, neuropathy and nephropathy) are directly correlated to blood glucose control. A clinical trial is currently underway in the UK to determine if this link also holds true to Type II diabetes. A positive result is reasonable to anticipate, and with it will come a desire for agents that improve the ability for the patient with diabetes to control blood glucose levels tightly. In addition, a standard of care for diabetes is being developed by the US government in coordination with care-givers and the pharmaceutical industry. Thus, there is clearly a need for agents that truly are able to tightly control blood glucose levels in the normal range.

Glucagon-like peptide-1 (GLP-1) was first identified in 1987 as a incretin hormone, a peptide secreted by the gut upon ingestion of food. GLP-1 is secreted by the L-cells of the intestine after being proteolytically processed from the 160 amino acid precursor protein, preproglucagon. Cleavage of preproglucagon first yields GLP-1, a 37 amino acid peptide, GLP-1(1–37)OH, that is poorly active. A subsequent cleavage at the 7-position yields biologically active GLP-1(7–37)OH. Approximately 80% of the GLP-1(7–37) OH that is synthesized is amidated at the C-terminal after removal of the terminal glycine residue in the L-cells. The biological effects and metabolic turnover of the free acid GLP-1(7–37)OH, and the amide, GLP-1 (7–36)NH$_2$, are indistinguishable.

GLP-1 is known to stimulate insulin secretion (insulinotropic action) causing glucose uptake by cells which decreases serum glucose levels (see, e g., Mojsov, S., *Int. J. Peptide Protein Research,* 40:333–343 (1992)). Numerous GLP-1 analogs demonstrating insulinotropic action are known in the art. These variants and analogs include, for example, GLP-1(7–36), Gln$^9$-GLP-1(7–37), D-Gln$^9$-GLP-1(7–37), acetyl-Lys$^9$-GLP-1(7–37), Thr$^{16}$-Lys$^{18}$-GLP-1(7–37), and Lys$^{18}$-GLP-1(7–37). Derivatives of GLP-1 include, for example, acid addition salts, carboxylate salts, lower alkyl esters, and amides (see, e.g., WO91/11457 (1991); EP 0 733,644 (1996); and U.S. Pat. No. 5,512,549 (1996)). It has also been demonstrated that the N-terminal histidine residue (His 7) is very important to insulinotropic activity of GLP-1 (Suzuki, S., et al. *Diabetes Res.; Clinical Practice* 5 (Supp. 1):S30 (1988).

Multiple authors have demonstrated the nexus between laboratory experimentation and mammalian, particularly human, insulinotropic responses to exogenous administration of GLP-1, particularly GLP-1 (7–36)NH$_2$ and GLP-1 (7–37) [see, e.g., Nauck, M. A., et al., *Diabetologia,* 36:741–744 (1993); Gutniak, M., et al., *New England J. of Medicine,* 326(20):1316–1322 (1992); Nauck, M. A., et al., *J. Clin. Invest.,* 91:301–307 (1993); and Thorens, B., et al., *Diabetes,* 42:1219–1225 (1993)].

GLP-1 based peptides hold great promise as alternatives to insulin therapy for patients with diabetes who have failed on sulfonylureas. GLP-1 has been studied intensively by academic investigators, and this research has established the following for patients with type II diabetes who have failed on sulfonylureas:

1) GLP-1 stimulates insulin secretion, but only during periods of hyperglycemia. The safety of GLP-1 compared to insulin is enhanced by this property of GLP-1 and by the observation that the amount of insulin secreted is proportional to the magnitude of the hyperglycemia. In addition, GLP-1 therapy will result in pancreatic release of insulin and first-pass insulin action at the liver. This results in lower circulating levels of insulin in the periphery compared to subcutaneous insulin injections. 2) GLP-1 suppresses glucagon secretion, and this, in addition to the delivery of insulin via the portal vein helps suppress the excessive hepatic glucose output in diabetic patients. 3) GLP-1 slows gastric emptying which is desirable in that it spreads nutrient absorption over a longer time period, decreasing the post-prandial glucose peak. 4) Several reports have suggested that GLP-1 may enhance insulin sensitivity in peripheral tissues such as muscle and fat. 5) Finally, GLP-1 has been shown to be a potential regulator of appetite.

Meal-time use of GLP-1 based peptides offers several advantages over insulin therapy. Insulin therapy requires blood glucose monitoring, which is both expensive and painful. The glucose-dependency of GLP-1 provides an enhanced therapeutic window in comparison to insulin, and should minimize the need to monitor blood glucose. Weight gain also can be a problem with intensive insulin therapy, particularly in the obese type II diabetic patients.

The therapeutic potential for native GLP-1 is further increased if one considers its use in patients with type I diabetes. A number of studies have demonstrated the effectiveness of native GLP-1 in the treatment of insulin dependent diabetes mellitus (IDDM). Similar to NIDDM patients, GLP-1 is effective in reducing fasting hyperglycemia through its glucagonostatic properties. Additional studies have indicated that GLP-1 also reduces postprandial glycemic excursions in IDDM, most likely through a delay in gastric emptying. These observations indicate that GLP-1 is may be useful as a treatment in IDDM as well as in NIDDM.

However, the biological half-life of native GLP-1 molecules which are affected by the activity of dipeptidyl-peptidase IV (DPP IV) is quite short. For example, the biological half-life of GLP-1(7–37)OH is a mere 3 to 5 minutes (U.S. Pat. No. 5,118,666). Therefore extended-action GLP-1 based peptides are needed to enhance glycemic control during the night while minimizing the risk of hypoglycemia.

In one embodiment, the present invention provides GLP-1 analogs that have extended time action relative to native GLP-1, show resistance to the action of DPP-IV, and retain affinity for the GLP-1 receptor.

SUMMARY OF THE INVENTION

The invention includes a GLP-1 compound of the formula:

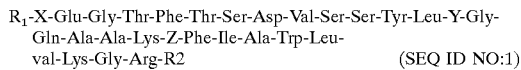

$R_1$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-val-Lys-Gly-Arg-R2    (SEQ ID NO:1)

or a pharmacuetically accetable salt thereof, wherein:
$R_1$ is selected from the group consisting of His, D-histidine, desamino-histidine, 2-amino-histidine, β-hydroxy-histidine, homohistidine, alpha-fluoromethyl-histidine, and alpha-methyl-histidine;
X is selected from the group consisting of Met, Asp, Lys, Thr, Leu, Asn, Gln, Phe, Val, and Tyr
Y and Z are independently selected from the group consisting of Glu, Gln, Ala, Thr, Ser, and Gly, and;
$R_2$ is selected from the group consisting of $NH_2$, and Gly-OH; provided that, if $R_1$ is His, X is Val, Y is Glu, and Z is Glu, then $R_2$ is $NH_2$.

Also provided by the present invention are pharmaceutical compositions comprising a GLP-1 compound of the present invention in combination with one or more pharmaceutically acceptable carriers, diluents, or excipients.

The present invention further provides a method of treating diabetes which comprises administering to a mammal in need of such treatment an effective amount of a GLP-1 compound of the present invention.

DETAILED DESCRIPTION OF THE INVENTION

In one embodiment, the present invention provides novel, biologically-active GLP-1 based peptides. It should be noted that this specification uses the nomenclature scheme that has developed around processed forms of GLP-1. In this scheme, the amino terminus of native GLP-1(7–37)OH has been assigned number 7 and the carboxy terminus number 37. Therefore, $R_1$ of SEQ ID NO: 1 corresponds to residue 7 of GLP-1(7–37)OH. Likewise X in SEQ ID NO: 1 corresponds to residue 8 of GLP-1(7–37)OH and Y corresponds to residue 21 and so forth. Moreover, all amino acids referred to in this specification are in the L form, unless otherwise specified.

In a preferred embodiment, $R_1$ is His, and Y and Z are Glu. Another preferred group is when $R_1$ is His, $R_2$ is Gly-OH, and any one or more of X, Y, and Z differ from the residues present in native GLP-1(7–37)OH. Another preferred group is when $R_1$ is His, X is Met, Asp, Lys, Thr, Leu, Asn, Gln, Phe or Typ, Y and Z are Glu, and $R_2$ is Gly-OH.

Given the sequence information herein disclosed and the state of the art in solid phase protein synthesis, GLP-1 analogs can be obtained via chemical synthesis. However, it also is possible to obtain a GLP-1 analog by fragmenting proglucagon using, for example, proteolytic enzymes. Moreover, recombinant DNA techniques may be used to express GLP-1 analogs of the invention.

The principles of solid phase chemical synthesis of polypeptides are well known in the art and may be found in general texts in the area such as Dugas, H. and Penney, C., *Bioorganic Chemistry* (1981) Springer-Verlag, New York, pgs. 54–92, Merrifield, J. M., *Chem. Soc.*, 85:2149 (1962), and Stewart and Young, *Solid Phase Peptide Synthesis*, pp. 24–66, Freeman (San Francisco, 1969).

For example, a GLP-1 analog of the invention may be synthesized by solid-phase methodology utilizing an Applied Biosystems 430A peptide synthesizer (Applied Biosystems, Inc., 850 Lincoln Center Drive, Foster City, Calif. 94404) and synthesis cycles supplied by Applied Biosystems. Boc amino acids and other reagents are commercially available from Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asp, Gln, and Arg are coupled using preformed hydroxy benzotriazole esters. The following side chain protecting groups may be used:

Arg, Tosyl
Asp, cyclotlexyl
Glu, cyclohexyl
Ser, Benzyl
Thr, Benzyl
Tyr, 4-bromo carbobenzoxy Boc deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at zero degrees centigrade or below, preferably –20° C. for thirty minutes followed by thirty minutes at 0° C. After removal of the HF, the peptide/resin is washed with ether, and the peptide extracted with glacial acetic acid and lyophilized.

The preparation of protected, unprotected, and partially protected GLP-1 has been described in the art. See U.S. Pat. Nos. 5,120,712 and 5,118,666, herein incorporated by reference, and Orskov, C., et al., *J. Biol. Chem.*, 264 (22):12826–12829 (1989) and WO 91/11457 (Buckley, D. I., et al., published Aug. 8, 1991).

Likewise, the state of the art in molecular biology provides the ordinarily skilled artisan another means by which GLP-1 analogs can be obtained. Although GLP-1 analogs may be produced by solid phase peptide synthesis, recombinant methods, or by fragmenting glucagon, recombinant methods may be preferable because higher yields are possible. The basic steps in the recombinant production of a GLP-1 analog are:

a) isolating a natural DNA sequence encoding GLP-1 or constructing a synthetic or semi-synthetic DNA coding sequence for GLP-1, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 intermediate, and e) recovering and purifying the recombinantly produced protein.

As previously stated, the coding sequences for GLP-1 analogs may be wholly synthetic or the result of modifications to the larger, native glucagon-encoding DNA. A DNA sequence that encodes preproglucagon is presented in Lund, et al., *Proc. Natl. Acad. Sci. U.S.A.* 79:345–349 (1982) and may be used as starting material in the recombinant production of a GLP-1 analog by altering the native sequence to achieve the desired results.

Synthetic genes, the in vitro or in vivo transcription and translation of which results in the production of a GLP-1 analog, may be constructed by techniques well known in the art. Owing to the natural degeneracy of the genetic code, the skilled artisan will recognize that a sizable yet definite number of DNA sequences may be constructed which encode GLP-1 intermediates.

The methodology of synthetic gene construction is well known in the art. See Brown, et al. (1979) *Methods in Enzymology*, Academic Press, N.Y., Vol. 68, pgs. 109–151. DNA sequences that encode GLP-1 intermediates can be designed based on the amino acid sequences herein disclosed. Once designed, the sequence itself may be generated using conventional DNA synthesizing apparatus such as the Applied Biosystems Model 380A or 380B DNA synthesizers (Applied Biosystems, Inc., 850 Lincoln Center Drive, Foster City, Calif. 94404).

To effect the expression of a biologically-active GPL-1 analog, one inserts the engineered synthetic DNA sequence in any one of many appropriate recombinant DNA expression vectors through the use of appropriate restriction endonucleases. See generally Maniatis et al. (1989) *Molecular Cloning; A Laboratory Manual,* Cold Springs Harbor Laboratory Press, N.Y., Vol. 1–3. Restriction endonuclease cleavage sites are engineered into either end of the DNA encoding the GLP-1 analog to facilitate isolation from, and integration into, known amplification and expression vectors. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein of interest. The coding sequence must be positioned so as to be in proper reading frame with the promoter and ribosome binding site of the expression vector, both of which are functional in the host cell in which the protein is to be expressed.

To achieve efficient transcription of the coding region, it must be operably associated with a promoter-operator region. Therefore, the promoter-operator region of the gene is placed in the same sequential orientation with respect to the ATG start codon of the coding region.

A variety of expression vectors useful for transforming prokaryotic and eukaryotic cells are well known in the art. See *The Promega Biological Research Products Catalogue* (1992) (Promega Corp., 2800 Woods Hollow Road, Madison, Wis., 53711–5399); and *The Stratagene Cloning Systems Catalogue* (1992) (Stratagene Corp., 11011 North Torrey Pines Road, La Jolla, Calif., 92037). Also, U.S. Pat. No. 4,710,473 describes circular DNA plasmid transformation vectors useful for expression of exogenous genes in *E. coli* at high levels. These plasmids are useful as transformation vectors in recombinant DNA procedures and:

(a) confer on the plasmid the capacity for autonomous replication in a host cell;

(b) control autonomous plasmid replication in relation to the temperature at which host cell cultures are maintained;

(c) stabilize maintenance of the plasmid in host cell populations;

(d) direct synthesis of a protein prod. indicative of plasmid maintenance in a host cell population;

(e) provide in series restriction endonuclease recognition sites unique to the plasmid; and (f) terminate mRNA transcription.

These circular DNA plasmids are useful as vectors in recombinant DNA procedures for securing high levels of expression of exogenous genes.

Having constructed an expression vector for a GLP-1 analog, the next step is to place the vector into a suitable cell and thereby construct a recombinant host cell useful for expressing a GLP-1 analog. Techniques for transforming cells with recombinant DNA vectors are well known in the art and may be found in such general references as Maniatis, et al. supra. Host cells made be constructed from either eukaryotic or prokaryotic cells. Eukaryotic host cells are capable of carrying out post-translational glycosylations on expressed proteins and some are capable of secreting the desired protein into the culture medium.

Prokaryotic host cells generally produce the protein at higher rates, are easier to culture but are not capable of glycosylating the final protein. Proteins which are expressed in high-level bacterial expression systems may aggregate in granules or inclusion bodies which contain high levels of the overexpressed protein. Such protein aggregates must be solubilized, denatured and refolded using techniques well known in the art. See Kreuger, et al. (1990) in *Protein Folding,* Gierasch and King, eds., pgs 136–142, American Association for the Advancement of Science Publication No. 89-18S, Washington, D.C.; and U.S. Pat. No. 4,923,967.

Regardless of the methods used to produce a GLP-1 analog, purification of the protein generally will be required. Methods for purifying proteins are well known in the art and include conventional chromatography, including ion and cation exchange, hydrophobic interaction, and immunoaffinity chromatographic media. The amino acid sequences herein disclosed in conjunction with well known protein purification methods will enable the ordinarily skilled artisan to purify GLP-1 analogs claimed herein.

The present invention also includes salt forms of GLP-1 analogs. A GLP-1 analog of the invention may be sufficiently acidic or sufficiently basic to react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. Salt forms of GLP-1 analogs are particularly preferred. Of course, when the compounds of this invention are used for therapeutic purposes, those compounds may also be in the form of a salt, but the salt must be pharmaceutically acceptable.

The ability of a GLP-1 analog to stimulate insulin secretion may be determined by providing a GLP-1 analog to cultured animal cells, such as the RIN-38 rat insulinoma cell line, and monitoring the release of immunoreactive insulin (IRI) into the media. Alternatively one can inject a GLP-1 analog into an animal and monitor plasma levels of immunoreactive insulin (IRI).

The presence of IRI is detected through the use of a radioimmunoassay which can specifically detect insulin. Any radioimmunoassay capable of detecting the presence of IRI may be employed; one such assay is a modification of the method of Albano, J. D. M., et al., *Acta Endocrinol.,* 70:487–509 (1972). In this modification, a phosphate/albumin buffer with a pH of 7.4 is employed. The incubation is prepared with the consecutive addition of 500 $\mu$l of phosphate buffer, 50 $\mu$l of perfusate sample or rat insulin standard in perfusate, 100 $\mu$l of anti-insulin antiserum (Wellcome Laboratories; 1:40,000 dilution), and 100 $\mu$l of [$^{125}$I] insulin, giving a total volume of 750 $\mu$l in a 10×75 mm disposable glass tube. After incubation for 2–3 days at 4° C., free insulin is separated from antibody-bound insulin by charcoal separation. The assay sensitivity is 1–2 uU/mL. In order to measure the release of IRI into the cell culture medium of cells grown in tissue culture, one preferably incorporates radioactive label into proinsulin. Although any radioactive label capable of labeling a polypeptide can be used, it is preferable to use $^3$H leucine in order to obtain labeled proinsulin.

To determine whether a GLP-1 analog has insulinotropic properties may also be determined by pancreatic infusion. The in situ isolated perfused rat pancreas assay is a modification of the method of Penhos, J. C., et al., *Diabetes,* 18:733–738 (1969). Fasted male Charles River strain albino rats, weighing 350–600 g, are anesthetized with an intraperitoneal injection of Amytal Sodium (Eli Lilly and Co.: 160 ng/kg). Renal, adrenal, gastric, and lower colonic blood vessels are ligated. The entire intestine is resected except for about four cm of duodenum and the descending colon and rectum. Therefore, only a small part of the intestine is perfused, minimizing possible interference by enteric substances with glucagon-like immunoreactivity. The perfusate is a modified Krebs-Ringer bicarbonate buffer with 4% dextran T70 and 0.2% bovine serum albumin (fraction V), and is bubbled with 95% $O_2$ and 5% $CO_2$. A nonpulsatile flow, 4-channel roller bearing pump (Buchler polystatic, Buchler Instruments Division, Nuclear-Chicago Corp.) is used, and a switch from one perfusate source to another is accomplished by switching a 3-way stopcock. The manner in which perfusion is performed, monitored, and analyzed follow the method of Weir, G. C., et al., *J. Clin. Investigat.* 54:1403–1412 (1974), which is hereby incorporated by reference.

The present invention also provides pharmaceutical compositions comprising a GLP-1 analog of the present invention in combination with a pharmaceutically acceptable carrier, diluent, or excipient. Such pharmaceutical compositions are prepared in a manner well known in the pharmaceutical art, and are administered individually or in combination with other therapeutic agents, preferably via parenteral routes. Especially preferred routes include intramuscular and subcutaneous administration.

Parenteral daily dosages, preferably a single, daily dose, are in the range from about 1 $\mu$g/kg to about 1,000 $\mu$g/kg of body weight, although lower or higher dosages may be administered. The required dosage will depend upon the severity of the condition of the patient and upon such criteria as the patient's height, weight, sex, age, and medical history.

In making the compositions of the present invention, the active ingredient, which comprises at least one protein of the present invention, is usually mixed with an excipient or diluted by an excipient. When an excipient is used as a diluent, it may be a solid, semi-solid, or liquid material which acts as a vehicle, carrier, or medium for the active ingredient.

In preparing a formulation, it may be necessary to mill the active compound to provide the appropriate particle size prior to combining with the other ingredients. If the active protein is substantially insoluble, it ordinarily is milled to particle size of less than about 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, trehalose, sorbitol, mannitol, starches, gum acacia, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form with each dosage normally containing from about 50 $\mu$g to about 100 mg, more usually from about 1 mg to about 10 mg of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient.

For the purpose of parenteral administration, compositions containing a protein of the present invention preferably are combined with distilled water and the pH is adjusted to about 6.0 to about 9.0.

Additional pharmaceutical methods may be employed to control the duration of action. Controlled release preparations may be achieved by the use of polymers to complex or absorb a compound of the present invention. The controlled delivery may be exercised by selecting appropriate macromolecules (for example, polyesters, polyamino acids, polyvinylpyrrolidone, ethylenevinyl acetate, methylcellulose, carboxymethylcellulose, and protamine sulfate) and the concentration of macromolecules as well as the methods of incorporation in order to control release.

Another possible method to control the duration of action by controlled release preparations is to incorporate a protein of the present invention into particles of a polymeric material such as polyesters, polyamino acids, hydrogels, poly (lactic acid) or ethylene vinylacetate copolymers.

Alternatively, instead of incorporating a compound into these polymeric particles, it is possible to entrap a compound of the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in *Remington's Pharmaceutical Sciences* (1980).

Similarly, the present invention provides a method for treating diabetes or hyperglycemia in a mammal, preferably a human, in need of such treatment comprising administering an effective amount of a GLP-1 analog or composition of the present invention, to such a mammal.

By way of illustration, the following examples are provided to help describe how to make and practice the various embodiments of the invention. These example are in no way meant to limit the scope of the invention.

EXAMPLE 1

Synthesis of Met-8 GLP-1(7–36)NH$_2$

Met-8 GLP-1(7–36)NH$_2$ was produced by solid phase peptide chemistry on an Applied Biosystems (ABI) 460A peptide synthesizer using a MBHA resin (Applied Biosystems Inc., lot # A1A023, 0.77 mmol/g). All amino acids had their a-amino groups protected by the tert-butyloxycarbonyl (t-Boc) group. Those with reactive side chains had them protected as follows: Arg(Tos); Lys(Cl-Z); Trp(CHO); Glu (CHex); Tyr(Br-Z); Ser(Bzl); Asp(OBzl); Thr(Bzl).

The protected amino acids were activated in dichloromethane (DCM) with one half an equivalent of dicyclohexylcarbodiimide (DCC) per equivalent of amino acid to give the symmetric anhydride of the amino acid. However, arginine, glutamine, and glycine residues were activated by forming the 1-hydroxybenzotriazole (HOBt) esters of these amino acids (1:1:1 equivalents of amino acid, HOBt, and DCC in dimtethylformamide (DMF)).

Residues were sequentially connected from the C-terminal towards the N-terminal end with a series of coupling and deprotection cycles. A coupling cycle consisted of the activated amino acid undergoing nucleophilic substitution by the free primary amine of the previously coupled amino acid. Deprotection was the removal of the N-terminal blocking group Boc with anhydrous trifluoroacetic acid (TFA). This generated a free amine group after neutralization with diisopropylethylamine (DIEA).

The synthesis scale was 0.5 mmol. The concentration of functional sites on the MBHA-resin was 0.77 mmol/g; 649 mg of resin was used. A two fold molar excess of the symmetric anhydride was used for all of the amino acids. The C-terminal Arginine was coupled to the MBHA-resin via standard protocols. All residues were double-coupled. That is each residue was coupled to the resin twice. The second coupling was performed without a Boc deprotection step prior to re-addition of the amino acid. This helped to completely react all of the free amine groups on the resin. The tryptophan residue was quadruple coupled. After the second coupling step of each double-coupling cycle the N-terminal Boc croups were removed with anhydrous TFA and neutralized with DIEA.

The formyl side chain blocking group on the tryptophan residue was removed with piperidine in DMF prior to cleaving the peptide from the resin. After the peptidyl-resin was transferred to a 50 ml sintered glass funnel, it was washed several times with DCM and DMF. Then 3–5 ml of a 50/50 piperidine/DMF solution was added to the peptide-resin so that it was just covered. After 5 minutes the piperidine/ DMF was removed by vacuum and 3–5 ml of piperidine/DMF was added. After 10 minutes, the piperidine/DMF again was removed by vacuum filtration and 15–20 ml of piperidine/DMF was added. After 15 minutes the piperidine/DMF was removed and the peptidyl-resin washed with DMF several times followed by DCM. The peptidyl-resin was then placed into a vacuum oven (no heat) to complete solvent removal.

Once the amino acids were sequentially coupled, and the formyl group removed, the peptide was liberated from the resin by hydrolysis with liquid hydrofluoric acid (HF) at 0° C. for one hour using a Teflon reaction vessel. In the process of liberating the peptide, the C terminal hydroxide was displaced with an amide group from the MBHA-resin (see Matseuda and Stewart, Peptides 2:45 (1981)). For every gram of peptidyl-resin, 1 ml of m-cresol scavenger was added and 10 ml of liquid HF used. The scavenger prevented the reattachment of side chain blocking groups (released as carbocations) to the peptide. After one hour, the HF was removed by vacuum leaving a slurry of peptide, resin, and m-cresol.

The peptide was then precipitated in the HF reaction vessel with ice cold diethyl ether. The precipitate was transferred to a 150 ml sintered glass funnel along with several ether rinses. The peptide/resin physical mixture was washed several times with cold ether to remove residual HF and m-cresol. The second step was to extract the peptide away from the resin using 10% acetic acid in water (v/v) Vacuum filtration into a clean round bottom flask yielded a crude peptide solution.

EXAMPLE 2

Purification

The crude peptide solution obtained in Example 1 was run on reverse-phase analytical HPLC at pH 2.3. The chromatogram showed a major peak indicating that an appreciable amount of the desired product was formed and that preparative purification was warranted.

The entire crude peptide solution was run on preparative reverse phase HPLC at pH 2 under the following conditions:

Buffers: A=0.1% TFA, 10% acetonitrile B=0.1% TFA, 50% acetonitrile

Column: Vydac C18 (2.2×25 cm)

Temperature: approximately 20° C.

Detector: 280 nm

Flow: 2.0 ml/min

Gradient: 25% B to 100% B over 1,000 minutes

The title peptide eluted at approximately 34% acetonitrile as identified by analytical HPLC and electrospray mass spectroscopy. The approximate yield was 125 mg of 60% purity by analytical HPLC at pH 2.3.

This crude preparation was then run on preparative reverse phase HPLC at pH 7.7 under the following conditions:

Buffers: A=0.1M $(NH_4)HCO_3$, 10% acetonitrile B=A, 50% acetonitrile

Column: Vydac C18 (2.2×25 cm)

Temperature: approximately 20° C.

Detector: 280 nm

Flow: 2.0 ml/min

Gradient: 35% B to 70% B over 1,000 minutes

The title peptide eluted between 32% and 37% acetonitrile as identified by analytical HPLC. The approximate yield was 10%.

EXAMPLE 3

Synthesis of Thr-8 GLP-1(7–37)OH

Thr-8 GLP-1(7–37)OH was prepared in substantial accordance with Examples 1 and 2, except that the peptide was released from the solid phase such that the C-terminal hydroxyl group remained.

EXAMPLE 4

In vitro Receptor Binding Assay a) Rat, GLP-1 receptor, membrane preparation:

The published DNA sequence for the rat GLP-1 receptor (Thorens B., et. al. *Proc. Natl. Acad. Sci. U.S.A.* 89:8641–8645 (1992) and the dihydrofolate reductase resistance marker gene were used in conjunction with PCR techniques to construct an expression vector. The DXB-11 variant of the chinese hamster ovary (CHO) cell line was transformed with the vector, resulting in a recombinant CHO cell line that expressed the rat GLP-1 membrane receptor.

Cells were grown and harvested, and a membrane preparation was obtained by first washing the cells with PBS buffer, then twice washing with cold buffer (25 mM HEPES, 2 mM $MgCl_2$, 1L mM EDTA, 20 µg/ml Leupeptin, 1 mM PMSF, 2µg/ml Aprotinin, 50 µg/ml Trypsin Inhibitor, pH 8.0) and resuspending in buffer. The cell suspension was lysed in a glass Teflon homogenizer, and the resulting sample was then centrifuged at 35,300× g for 30 minutes at 4° C. The supernatant was removed, and the pellet was resuspended in cold buffer and homogenized. Aliquots were stored at −80° C.

b) Cyclic AMP (cAMP) Assay:

A sample of the membrane preparation was pre-incubated with a test compound or a control compound in buffer (25 mM HEPES, 0.2% (w/v) BSA, pH 7.6) at 32° C. for 10 minutes. Reaction buffer (final concentration: 25 mM HEPES, 0.2% (w/v) BSA, 2.6 mM Mg, 0.8 mM ATP, 0.1 mM GTP, 5 mM creatine phosphate, creatine kinase 50 U/ml, 0.2 mM IBMX, pH 7.6) was added and incubated for an additional 30 minutes. Incubations were stopped by adding 10 mM EDTA.

Production of cAMP was assayed using a fluorescent tracer-immuno assay method. In brief, after the incubation was stopped, fluorescent tracer (cAMP-b phycoerythrin conjugate) was added followed by the addition of affinity purified anti-cAMP rabbit antiserum. After incubation at room temperature for 45 minutes, anti-rabbit IgG coated assay beads were added and incubated for an additional 15 minutes. Plates were then evacuated and read on a Pandex PFCIA reader.

In this assay, a known insulinotropic agent such as GLP-1(7–37)OH showed decreasing fluorescent intensity due to increased cAMP concentration. Fluorescent intensity values were correlated to rate of cAMP production (pmol/min/mg). Conversely, agents having no insulinotropic action failed to stimulate production of cAMP and therefore showed no decrease in fluorescent intensity. Percent receptor affinities are shown below:

| | |
|---|---|
| GLP-1(7–37)OH | 100% |
| Met-8 GLP-1(7–36)$NH_2$ | 16.6% ± 5.8% |
| Thr-8 GLP-1(7–37)OH | 2.8% ± 0.7% |

---

I claim:

1. A glucagon-like peptide-1 compound of the formula:

$R_1$-Met-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-$R_2$ (SEQ ID NO: 2)

or a pharmaceutically acceptable salt thereof, wherein:

$R_1$ is selected from the group consisting of His, D-histidine, desamino-histidine, 2-amino-histidine, β-hydroxy-histidine, homohistidine, alpha-fluoromethyl-histidine, and alpha-methyl-histidine;

Y is selected from the group consisting of Glu, Gln, Ala, Thr, Ser, and Gly;

Z is selected from the group consisting of Glu, Gln, Ala, Thr, Ser, and Gly, and;

$R_2$ is selected from the group consisting of $NH_2$, and Gly-OH.

2. The compound of claim 1 wherein $R_1$ is His, Y is Glu, Z is Glu, and $R_2$ is Gly-OH.

3. The compound of claim 1 wherein $R_1$ is His, Y is Glu, Z is Glu, and $R_2$ is $NH_2$.

4. A pharmaceutical formulation comprising a compound of claim 1, or a pharmaceutically acceptable salt thereof in combination with a pharmaceutically acceptable carrier, diluent, or excipient.

5. A pharmaceutical formulation comprising a compound of claim 2, or a pharmaceutically acceptable salt thereof in combination with a pharmaceutically acceptable carrier, diluent, or excipient.

6. A pharmaceutical formulation comprising a compound of claim 3, or a pharmaceutically acceptable salt thereof in combination with a pharmaceutically acceptable carrier, diluent, or excipient.

7. A method for treating diabetes in a mammal in need of such treatment comprising administering an effective amount of a compound of claim 1 to said mammal.

* * * * *

UNITED STATES PATENT AND TRADEMARK OFFICE
CERTIFICATE OF CORRECTION

PATENT NO.   :   5,981,488

DATED        :   November 9, 1999

INVENTOR     :   James Arthur Hoffmann

It is certified that an error appears in the above-identified patent and that said Letters Patent is hereby corrected as shown below:

Columns:

Description of Correction

Column 13, Lines 47 and 48, replace entire formula as printed with the following formula:

--- $R_1$-Met-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-$R_2$
(SEQ ID NO: 2) ---

Column 13, Line 62, replace "$R_1$ is His," with --- $R_1$ is His, X is Met, ---

Column 14, Line 45, replace "$R_1$ is His," with --- $R_1$ is His, X is Met, ---

Signed and Sealed this

Twenty-seventh Day of March, 2001

Attest:

NICHOLAS P. GODICI

Attesting Officer

*Acting Director of the United States Patent and Trademark Office*

SEQUENCE LISTING

<160> NUMBER OF SEQ ID NOS: 2

<210> SEQ ID NO 1
<211> LENGTH: 31
<212> TYPE: PRT
<213> ORGANISM: Artificial Sequence
<220> FEATURE:
<223> OTHER INFORMATION: Xaa at position 1 is chosen from His,
    D-histidine, desamino-histidine, 2-amino-histidine,
    beta-hydroxy-histidine, homohistidine,
    alpha-fluoromethyl-histidine, and
    alpha-methyl-histidine.
<220> FEATURE:
<223> OTHER INFORMATION: Xaa at position 2 is chosen from Met, Asp, Lys,
    Thr, Leu, Asn, Gln, Phe, Val and Tyr.
<220> FEATURE:
<223> OTHER INFORMATION: Xaa at position 15 is chosen from Glu, Gln,
    Ala, Thr, Ser, and Gly.
<220> FEATURE:
<223> OTHER INFORMATION: Xaa at position 21 is chosen from  Glu, Gln,
    Ala, Thr, Ser and Gly.
<220> FEATURE:
<223> OTHER INFORMATION: Arg at position 30 is amidated, if Gly at
    position 31 is absent.

```
<220> FEATURE:
<223> OTHER INFORMATION: Gly at position 31 may be absent.  If absent,
      Arg at position 30 is amidated.
<220> FEATURE:
<223> OTHER INFORMATION: Description of Artificial Sequence:Synthetic
      construct

<400> SEQUENCE: 1

Xaa Xaa Glu Gly Thr Phe Thr Ser Asp Val Ser Ser Tyr Leu Xaa Gly
 1               5                  10                  15

Gln Ala Ala Lys Xaa Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Xaa at position 1 is chosen from His,
      D-histidine, desamino-histidine,
      2-amino-histidine, beta-hydroxy-histidine,
      homohistidine, alpha-fluoromethyl-histidine, and
      alpha-methyl-histidine.
<220> FEATURE:
<223> OTHER INFORMATION: Xaa at position 15 is chosen from Glu, Gln,
      Ala, Thr, Ser, and Gly.
<220> FEATURE:
<223> OTHER INFORMATION: Xaa at position 21 is chosen from Glu, Gln,
      Ala, Thr, Ser, Gly.
<220> FEATURE:
<223> OTHER INFORMATION: Arg at position 30 is amidated, if Gly at
      position 31 is absent.
<220> FEATURE:
<223> OTHER INFORMATION: Gly at position 31 may be absent.  If absent,
      Arg at position 30 is amidated.
<220> FEATURE:
<223> OTHER INFORMATION: Description of Artificial Sequence:Synthetic
      construct

<400> SEQUENCE: 2

Xaa Met Glu Gly Thr Phe Thr Ser Asp Val Ser Ser Tyr Leu Xaa Gly
 1               5                  10                  15

Gln Ala Ala Lys Xaa Phe Ile Ala Trp Leu Val Lys Gly Arg Gly
            20                  25                  30
```